(12) United States Patent
Mauch

(10) Patent No.: US 9,050,439 B1
(45) Date of Patent: Jun. 9, 2015

(54) CATHETER LOADING DEVICE AND METHOD OF USING SAME

(71) Applicant: Medtronic Ardian Luxembourg S.a.r.l., Luxembourg (LU)

(72) Inventor: Kevin Mauch, Windsor, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/086,663

(22) Filed: Nov. 21, 2013

(51) Int. Cl.
*A61M 25/00* (2006.01)
*A61M 25/09* (2006.01)
*A61M 25/01* (2006.01)

(52) U.S. Cl.
CPC ..... *A61M 25/09041* (2013.01); *A61M 25/0172* (2013.01)

(58) Field of Classification Search
CPC .................... A61M 25/09041; A61M 25/0172
USPC .................. 604/510, 523, 533; 600/434, 585
See application file for complete search history.

(56) References Cited

U.S. PATENT DOCUMENTS

| 4,716,757 A * | 1/1988 | McGregor et al. ............... 72/387 |
| 7,011,635 B1 * | 3/2006 | Delay ............................ 600/585 |
| 7,951,092 B2 | 5/2011 | Jones et al. |

\* cited by examiner

*Primary Examiner* — Theodore Stigell
*Assistant Examiner* — Amber Stiles

(57) ABSTRACT

A catheter loading device includes a guidewire section, a catheter section, and a hinge that connects a proximal end of the guidewire section to a distal end of the catheter section. The guidewire section is rotatable relative to the catheter section about a rotation axis between a first position and a second position. When the guidewire section is in the first position, a longitudinal axis of a guidewire positioned in a channel of the guidewire section is aligned with a longitudinal axis of a lumen of a catheter positioned in a receiver of the catheter section. When the guidewire section is in the second position, the longitudinal axis of the guidewire positioned in the channel is not aligned with the longitudinal axis of the lumen of the catheter positioned in the receiver.

18 Claims, 5 Drawing Sheets

CATHETER LOADING DEVICE AND METHOD OF USING SAME

BACKGROUND

Medical guidewires are used in numerous catheterization procedures to aid in placing a catheter and/or prosthesis at a selected site within a body lumen. One of the more common uses of guidewires is in the catheterization of blood vessels for diagnostic or therapeutic purposes. These guidewires may be extremely slender. For example, some guidewires can have proximal ends that are about 0.008 inches (0.203 mm) in diameter. A proximal end of a guidewire can be inserted into a lumen of a distal end of a catheter, which can also have a relatively small diameter, e.g., about 0.0155 inches (0.39 mm). The catheter can then be fed along the guidewire such that it is directed to a desired location within a patient.

Inserting the guidewire into the lumen of the catheter is often difficult due to the small dimensions of the guidewire and the lumen, and the relatively delicate nature of these components. To align the guidewire with the lumen, physicians sometimes rest the tip of the catheter and proximal end of the guidewire on their index fingers as they load the wire into the catheter. Such a technique, however, may cause the proximal end of the guidewire to perforate a surgical glove, risking infection and requiring a change of gloves before completing the procedure. This technique may also cause damage to the catheter distal region wherein the guidewire could be incorrectly inserted causing the wire to perforate the catheter wall, leading to a patient safety risk.

Further, some types of catheters have curved sections proximate their distal ends. Steadying these curved ends and aligning them with guidewires can provide an even greater challenge to physicians.

SUMMARY

In one aspect, the present disclosure provides a catheter loading device that includes a guidewire section including a channel configured to receive a guidewire, where the channel extends along a channel axis from a free end of the guidewire section towards a proximal end of the guidewire section. The catheter loading device further includes a catheter section including a tubular receiver configured to slidably receive a catheter, where the receiver extends along a receiver axis in a proximal direction from a distal end of the catheter section; and a hinge rotatably connecting the proximal end of the guidewire section to the distal end of the catheter section, where the hinge defines a rotation axis transverse to the receiver axis. The guidewire section is rotatable relative to the catheter section about the rotation axis between a first position and a second position. When the guidewire section is in the first position, a longitudinal axis of a guidewire positioned in the channel is aligned with a longitudinal axis of a lumen of a catheter positioned in the receiver. When the guidewire section is in the second position, the longitudinal axis of the guidewire positioned in the channel is not aligned with the longitudinal axis of the lumen of the catheter positioned in the receiver.

In another aspect, the present disclosure provides a catheter that includes an elongate catheter body having a lumen extending therethrough from an open distal end of the catheter, where the lumen has a longitudinal axis; and a loading device mounted about the catheter body. The loading device includes a guidewire section having a channel configured to receive a guidewire, where the channel extends along a channel axis between a free distal end of the guidewire section and a proximal end of the guidewire section; a catheter section including a tubular receiver configured to slidably receive the catheter, where the receiver extends proximally along a receiver axis from a distal end of the catheter section; and a hinge rotatably connecting the proximal end of the guidewire section to the distal end of the catheter section, where the hinge defines a rotation axis transverse to the receiver axis. The guidewire section is rotatable about the rotation axis relative to the catheter section between a first position and a second position. When the guidewire section is in the first position and the catheter is positioned in the receiver and a guidewire is positioned in the channel, the longitudinal axis of the guidewire is aligned with a longitudinal axis of the catheter lumen. When the guidewire section is in the second position and the catheter is positioned in the receiver and a guidewire is positioned in the channel, the longitudinal axis of the guidewire is not aligned with the longitudinal axis of the lumen of the catheter.

In another aspect, the present disclosure provides a method that includes receiving a catheter having an elongate catheter body and a guidewire lumen extending therethrough from an open catheter distal end; and receiving a loading device that includes a guidewire section having a channel configured to receive a guidewire and a catheter section having a tubular receiver configured to receive the catheter body, where a proximal end of the guidewire section is connected to a distal end of the catheter section by a hinge that defines a rotation axis such that the guidewire section is rotatable about the rotation axis relative to the catheter section between a first position and a second position. The method further includes positioning the loading device on the catheter such that the catheter body is disposed within the receiver and the catheter distal end is located proximate the hinge; positioning a proximal end of a guidewire in the channel; and directing the proximal end of the guidewire into the open distal end of the catheter.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1A:
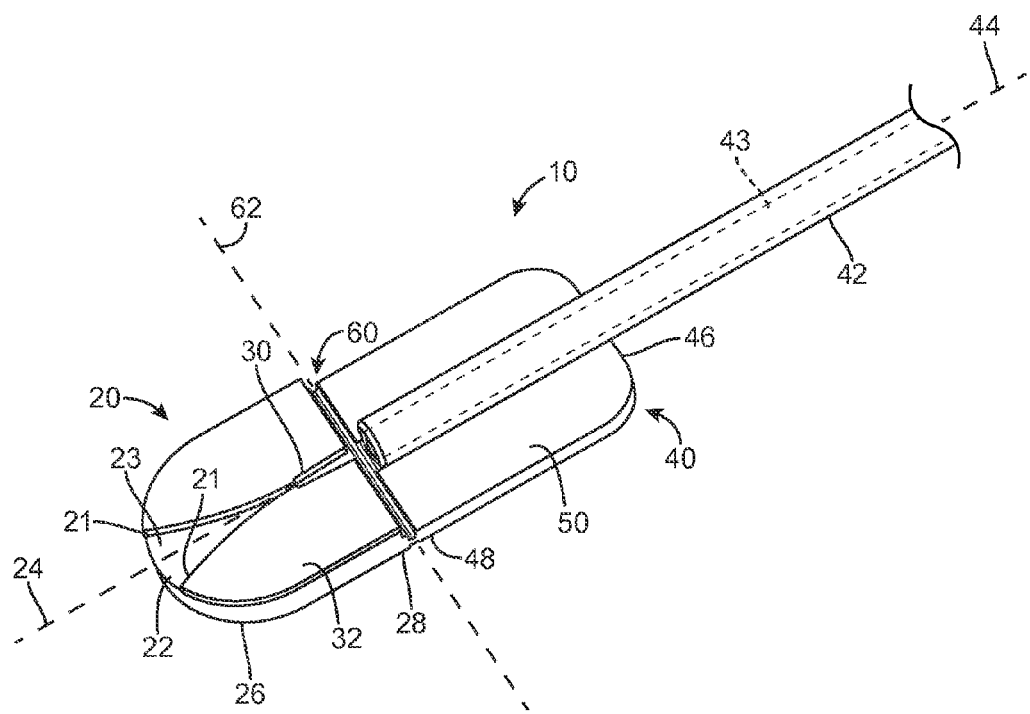
FIG. 1A is a perspective view of one embodiment of a catheter loading device.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention. As used herein, the terms "distal" and "proximal" define a position or direction with respect to a clinician or a clinician's control device (e.g., a handle of a catheter). The terms, "distal" and "distally" refer to a position distant from or in a direction away from a clinician or a clinician's control device. The terms "proximal" and "proximally" refer to a position near or in a direction toward a clinician or a clinician's control device.

One or more embodiments of the catheter loading device described herein can allow a physician to more easily direct a guidewire into a lumen of a catheter without the need for the physician to use a finger to steady the catheter. Further, in one or more embodiments, the catheter loading device can straighten a curved section of a catheter such that the physician is not required to straighten the curved section with one hand while attempting to direct the guidewire into the lumen of the catheter with the other hand.

In one or more embodiments, the catheter loading device includes a guidewire section, a catheter section, and a hinge that rotatably connects the guidewire section and the catheter section. The guidewire section may be a flat tab or flap rotatable about a rotation axis of the hinge relative to the catheter section between a first position and a second position. When in the second position, the guidewire section is essentially moved out of the way so that a receiver component of the catheter section can move along a body of a catheter. When in the first position, the catheter loading device is configured such that a longitudinal axis of a guidewire that is positioned in a channel of the guidewire section is aligned with a longitudinal axis of the catheter lumen that is positioned in the receiver component of the catheter section.

The catheter loading device of the present disclosure can be utilized with any suitable catheters and guidewires, e.g. wherein the catheter lumen is sized and shaped to slidably receive the medical guidewire. In some embodiments, the guidewires useable with the loading device can be adapted to be extended using an extension, as will be understood by those familiar with the field of medical guidewires.

Figure 1B:
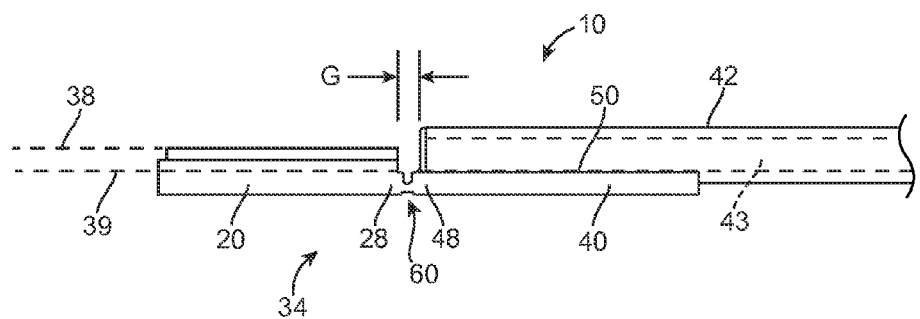
FIG. 1B is a side view of the catheter loading device of FIG. 1A with the device in a first position.

FIGS. 1A-E are various views of one embodiment of a catheter loading device 10. The device 10 includes a guidewire section 20, a catheter section 40, and a hinge 60 that connects the guidewire section to the catheter section. Hinge 60 may be a living or integral hinge, having a thin, flexible web of material that allows the more rigid connected sections 40, 60 to bend along the line of the hinge, herein defined as rotation axis 62. FIG. 1B shows an embodiment of loading device 10 with guidewire section 20 in first position 34 and wherein hinge 60 defines a gap G between the proximal end 28 of the guidewire section 20 and distal end 48 of catheter section 40. Gap G can range from zero, wherein receiver 42 abuts proximal end 28 of the guidewire section 20 to 0.040 inch (1.0 mm).

Figure 1C:
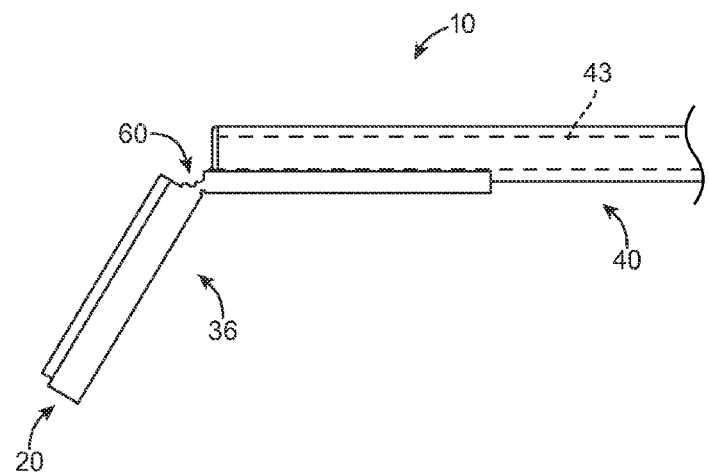
FIG. 1C is a side view of the catheter loading device of FIG. 1A with the device in a second position.
Figure 1D:
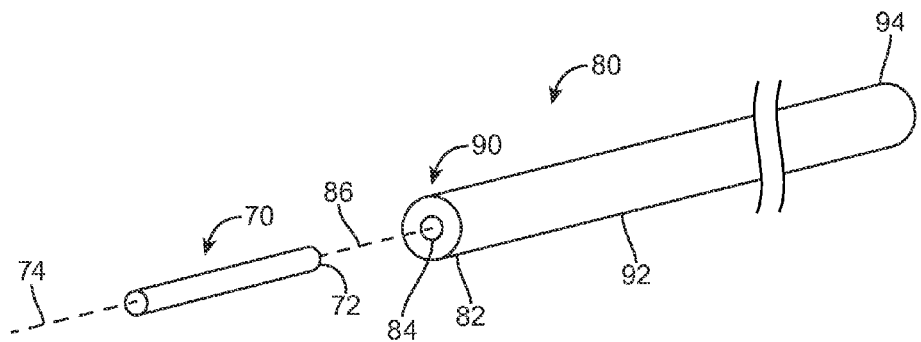
FIG. 1D is a schematic perspective view of a guidewire and a catheter positioned in the catheter loading device of FIG. 1A that is in the first position, where the catheter loading device is removed for clarity.
Figure 1E:
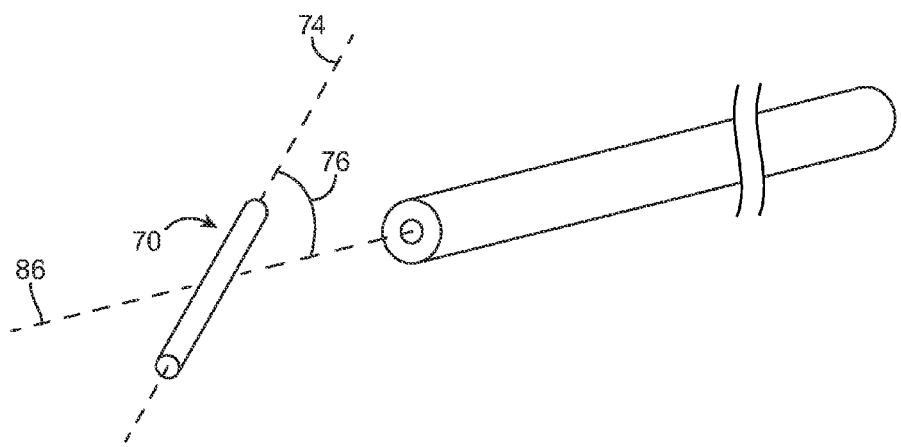
FIG. 1E is a schematic perspective view of the guidewire and the catheter of FIG. 1D positioned in the catheter loading device of FIG. 1A that is in the second position, where the catheter loading device is removed for clarity.

The guidewire section 20 may be a tab that includes a channel 22 configured to receive a guidewire 70 (shown in FIGS. 1D-E). The channel 22 extends along a channel axis 24 that extends between a free distal end 26 and a proximal end 28 of the guidewire section 20. The channel 22 can take any suitable shape that can slidably receive a guidewire. In some embodiments, the channel 22 has a width measured in a direction parallel to the rotation axis 62 that tapers (i.e., gets narrower) in a direction along the channel axis 24 from the free end 26 to the proximal end 28 of the guidewire section 20 as is shown in FIG. 1A. The wider portion of the tapered channel 22 can provide a larger area for a clinician to place a proximal end of a guidewire in the channel and guide the proximal end of the guidewire toward the catheter section 40 along the tapered portion of the channel. Further, the narrowing shape of the channel 22 can guide the end the guidewire toward the catheter section 40 and align the guidewire with the catheter lumen as is further described herein. In one or more alternative embodiments (not shown), the channel 22 can have a substantially constant width along the channel axis 24.

In one or more embodiments, such as the embodiment depicted in FIG. 1A, the channel 22 can have any suitably shaped sidewalls 21 and bottom surface 23. In some embodiments, the sidewalls 24 of the channel 22 can be transverse to a surface 32 of the guidewire section 20. In other embodiments, the sidewalls 21 can include sloped portions that guide a guidewire to the bottom surface 23 of the channel 22. The bottom surface 23 can also include a surface that is substantially parallel to the surface 32 of the guidewire section 20. In other embodiments, the bottom surface 23 of the channel 22 can include a curved surface.

As shown in FIGS. 1A-B, the channel 22 includes an optional recess 30 in the proximal end 28 of the guidewire section 20. Recess 30 can be any suitable shape such that it accommodates a distal end of a catheter (e.g., distal end 90 of catheter 80 of FIGS. 1D-E) and, in some embodiments, helps to retain the catheter distal tip in place as a guidewire is directed into a lumen of a catheter as is further described herein. In some embodiments, the recess 30 can be described as being formed into the surface 32 of the guidewire section 20 to any suitable depth. In some embodiments, the channel 22 is also formed into the surface 32 and has a first depth, and the recess 30 has a second depth that is greater than the first depth. Recess 30 also has a width greater than the width of channel 22 distal to recess 30. Thus, recess 30 provides a step or ledge against which catheter distal end 90 can abut when catheter 80 is disposed in a loading position in device 10. The first depth of channel 22 and the second depth of recess 30 can each be selected such that when guidewire section 20 is in the first position and catheter distal end 90 is positioned in recess 30, then the longitudinal axis 74 of guidewire 70 positioned in channel 22 is aligned with the longitudinal axis 86 of a catheter lumen 84.

The channel 22 can be formed in or on the surface 32 using any suitable technique. For example, the channel can be molded into the surface; alternatively, the channel can be stamped, machined or etched into the surface 32 after the guidewire section 20 is formed. The guidewire section 20 of catheter loading device 10 can include any suitable material or materials, e.g., polymers, metals, etc. Guidewire section 20 can be manufactured using any suitable technique, e.g., injection molding, extrusion molding, machining, 3D printing, etc.

Further, the guidewire section 20 can take any suitable shape in a plane parallel to its surface 32, e.g., rectangular, curvilinear, etc. The surface 32 of guidewire section 20 can also take any suitable shape. In some embodiments, the surface 32 is a substantially flat plane. In other embodiments, the surface 32 can include one or more beveled edges such that a clinician can more easily grasp the guidewire section 20.

Catheter section 40 includes a receiver component 42 having through lumen 43 configured to slidably receive a catheter (e.g., catheter 80 of FIGS. 1D-E). In the illustrated embodiment, catheter section 40 includes a flap or flat tab 50 extending from a distal end 48 to a free proximal end 46. In an alternative embodiment, the length of tab 50 may be only long enough to provide a connection between receiver 42 and hinge 60. The receiver 42 extends proximally along a receiver axis 44 from a distal end 48 to or beyond a free end 46 of the tab 50. The receiver 42 can take any suitable shape. In some embodiments, the receiver can take a tubular shape. In other embodiments, the receiver can take a substantially semi-cylindrical shape, with a portion of the receiver taking a cylindrical shape and another portion of the receiver taking a flattened shape, e.g., the portion of the receiver proximate a tab 50 of the catheter section 40. In some embodiments, the receiver lumen 43 is configured to slidably receive a catheter (e.g., catheter 80 of FIGS. 1D-E) such that the catheter loading device 10 can be moved along an elongate body of a catheter as is further described herein. Further, in some embodiments, the receiver 42 is configured to temporarily constrain or straighten a curved section of an elongate catheter body (e.g., curved section 288 of elongate body 292 of catheter 280 of FIG. 2A) while the curved section is disposed within receiver 42.

Any suitable technique can be used to form the receiver 42. In some embodiments, the receiver 42 can first be formed and then attached to the tab 50 of the catheter section 40 using any suitable attachment techniques. In other embodiments, the receiver 42 and catheter section 40 can be formed as a unitary element using any suitable technique, e.g., injection molding, extrusion molding, 3D printing, etc. In some embodiments, a channel (not shown) can be formed in the surface of tab 50 that is shaped to complement the shape of the receiver 42, and the receiver can be positioned within the channel and attached to the surface using any suitable technique.

The catheter section 40 and the receiver 42 can be made of any suitable material or materials, e.g., the same materials used for the guidewire section 20. In some embodiments, the catheter section 40 and the receiver 42 can include the same materials. In other embodiments, the catheter section 40 and the receiver 42 can include different materials. Further, the catheter section 40 can be manufactured using any suitable techniques, e.g., injection molding, extrusion molding, etc.

The catheter section 40 can take any suitable shape in a plane parallel to its surface 50, e.g., rectangular, curvilinear, etc. Tab 50 of catheter section 40 can also take any suitable shape. In some embodiments, the tab 50 is substantially flat. In other embodiments, tab 50 can include one or more beveled edges such that a clinician can more easily grasp the catheter section 40. In one or more embodiments, the catheter section 40 can be any suitable width or length. For example, in some embodiments, the tab 50 can have a width in a direction transverse to the receiver axis 44 that is no greater than a diameter of the receiver 42. In other embodiments, the catheter section 40 can be in the shape and size of the receiver 42.

The catheter section 40 is hingedly connected to the guidewire section 20 via the hinge 60. In the illustrated embodiment, hinge 60 rotatably connects proximal end 28 of the guidewire section 20 to distal end 48 of the catheter section 40. The hinge 60 defines the rotation axis 62. In some embodiments, rotation axis 62 is transverse to receiver axis 44.

The hinge 60 can include any suitable hinge. For example, in the illustrated embodiment, the hinge 60 is a living hinge that is formed as a unitary part of the guidewire section 20 and the catheter section 40. In some embodiments, the catheter loading device 10 can be formed as a single piece. In other embodiments, the guidewire section 20 and the catheter section 40 can be formed separately and then connected using a separate hinge 60. In some embodiments, the hinge 60 is biased to position the guidewire section 20 in a first position (e.g., first position 34 of FIG. 1B) with respect to catheter section 40.

The hinge 60 enables the guidewire section 20 and the catheter section 40 to be rotated relative to each other about the rotation axis 62 of the hinge. For example, as illustrated in FIGS. 1B-C, the guidewire section 20 is rotatable relative to the catheter section 40 about the rotation axis 62 between a first position 34 (FIG. 1B) and a second position 36 (FIG. 1C).

When the catheter loading device 10 has guidewire section 20 in the first position 34, device 10 is configured such that a longitudinal axis of a guidewire positioned in channel 22 is aligned with a longitudinal axis of a lumen of a catheter positioned in receiver 42 as is further described herein. Further, in some embodiments, when guidewire section 20 is in the second position 36, the device 10 is configured such that the longitudinal axis of the guidewire is not aligned with the longitudinal axis of the lumen of the catheter.

Further, in some embodiments, a plane 38 containing the surface 32 of the guidewire section 20 is substantially parallel to a plane 39 containing the top surface of tab 50 of the catheter section 40 when the guidewire section is in the first position 34 as shown in FIG. 1B. In this context, substantially parallel planes may mean planes that do not intersect at all or planes that may form an intersecting angle up to about 10 degrees.

FIG. 1D is a perspective view of a portion of a guidewire 70 and a catheter 80, where the guidewire is positioned in the channel 22 of the guidewire section 20 and the catheter is positioned in the receiver 42 of the catheter section 40. The device 10 is not included in this view to better show the alignment of the guidewire 70 and the catheter 80 when guidewire section 20 is in the first position (see, e.g., FIG. 1B). The guidewire 70 includes a proximal end 72 and defines a longitudinal axis 74. Catheter 80 includes an elongate catheter body 92 and a catheter lumen 84 extending within the catheter body from an open distal end 90 to a catheter proximal end 94. The catheter lumen 84 defines a longitudinal axis 86. The catheter 80 also defines a distal tip 82 proximate the distal end 90.

As shown in FIG. 1D, when guidewire section 20 is in the first position, the longitudinal axis 74 of guidewire 70 is aligned with the longitudinal axis 86 of catheter lumen 84. Although perfect collinear alignment of axes 74 and 86 is ideal, there is some tolerance for misalignment depending in part on the clearance between the proximal end of guidewire 70 and catheter open distal end 90. In some combinations of guidewire 70 and catheter 80, axes 74 and 86 may form a slight angle up to perhaps 10 degrees. Similarly, axes 74 and 86 may be parallel but slightly offset by perhaps a few thousandths of an inch.

When the device 10 is in the second position 36, the longitudinal axis 74 of the guidewire 70 is not aligned with the longitudinal axis 86 of the lumen of 84 of the catheter 80. As shown in FIG. 1E, in some embodiments, when the two axes are not aligned, the axes may form an angle 76 of at least 45 degrees.

Suitable dimensions for device 10 can be selected for use with regard to the intended catheters and guidewires to accomplish alignment of the guidewire axis 74 and the lumen axis 86 when guidewire section 20 is in the first position 34. For example, the thicknesses of the guidewire section 20 and the catheter section 40 in a direction transverse to surfaces 32 and 50 respectively can be selected such that axes 74 and 86 are aligned by device 10. Alternatively, the depth of the channel 22 in relation to the positioning of a centerline of receiver 42 relative to the top surface of tab 50 of the catheter section 40 can be selected such that the guidewire axis 74 and the lumen axis 86 are aligned.

Figure 2A:
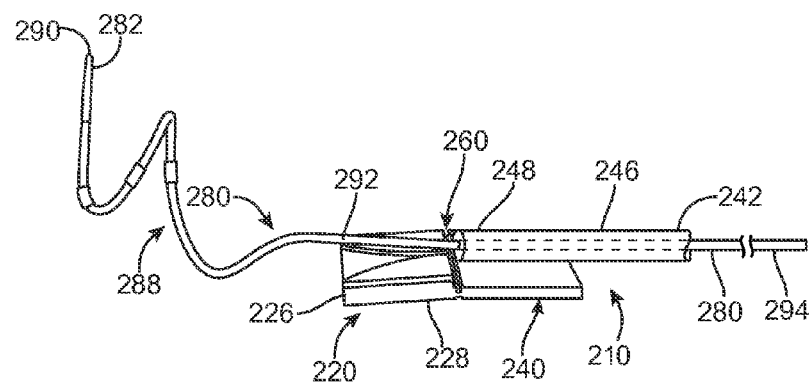
FIG. 2A is a perspective view of one embodiment of a catheter that includes one embodiment of a catheter loading device.
Figure 2B:
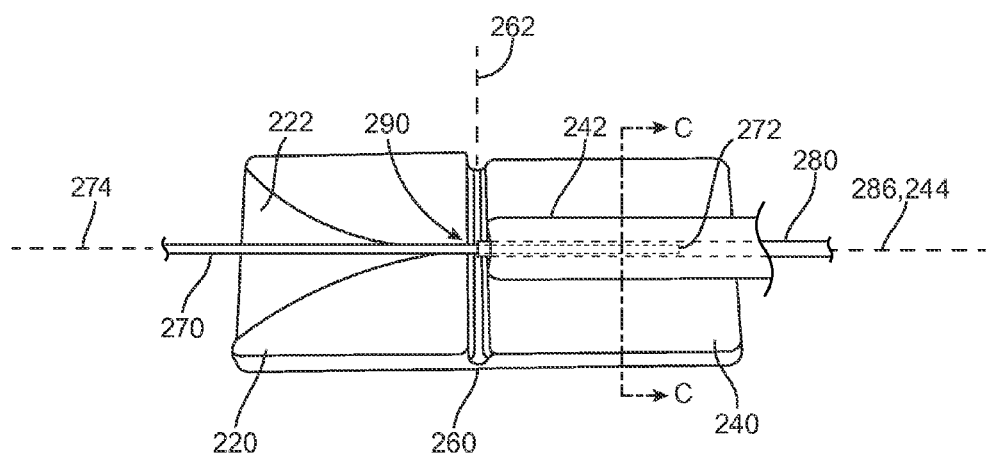
FIG. 2B is a perspective view of the catheter of FIG. 2A with a guidewire positioned in a channel of a guidewire section of the catheter loading device.
Figure 2C:
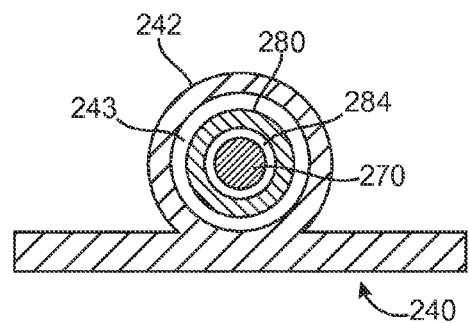
FIG. 2C is a transverse cross-section taken along line C-C of FIG. 2B.

As mentioned herein, in some embodiments the receiver 42 of the catheter section 40 is configured to slidably receive a catheter. For example, FIGS. 2A-C are views of a catheter 280 that includes a catheter loading device 210 mounted thereon. The catheter 280 includes an elongate catheter body 292, and a catheter lumen 284 extending within the catheter body from an open distal end 290 of the catheter. The catheter lumen 284 defines a longitudinal axis 286. The catheter 280 also includes a distal tip 282 portion proximate the distal end 290. The catheter 280 can include any suitable catheter.

In some embodiments, the catheter 280 can include a curved section 288 proximate the distal end 290 of the catheter. The curved section 288 can take any suitable shape, e.g., simple or compound curves, a helix or spiral, etc.

Catheter loading device 210 is mounted on catheter body 292. The device 210 can include any suitable catheter loading device described herein, e.g., device 10 of FIGS. 1A-E. The device 210 includes a guidewire section 220 including a channel 222 configured to receive a guidewire 270. The channel 222 extends along a channel axis (e.g., channel axis 24 of FIG. 1A) between a free end 226 and a proximal end 228 of the guidewire section 220.

The device 210 also includes a catheter section 240 that includes a receiver 242 configured to slidably receive the catheter 280. The receiver 242 extends proximally along a receiver axis (e.g., receiver axis 44 of FIG. 1A) from distal end 248. Receiver 242 may terminate at or extend proximally beyond tab free end 246 of catheter section 240. The length of receiver 242 may be selected as desired to provide sufficient engagement with catheter distal tip portion 282 to assist in the alignment and loading of guidewire 270 into catheter 280. The length of receiver 242 may also be selected to constrain all or a portion of catheter curved distal section 288 in a straightened configuration while guidewire 270 is loaded into catheter lumen 284.

A hinge 260 rotatably connects the proximal end 228 of the guidewire section 220 with the distal end 248 of the catheter section 240. The hinge 260 defines a rotation axis 262 transverse to longitudinal axis 286 of lumen 284 of catheter 280. All of the design considerations and possibilities regarding the guidewire section 20, the catheter section 40, and the hinge 60 of device 10 of FIGS. 1A-E apply equally to the guidewire section 220, the catheter section 240, and the hinge 260 of the device 210 of FIGS. 2A-C.

As illustrated in FIG. 2A, the guidewire section 220 is in a second position (e.g., second position 36 of FIG. 1C) such that the catheter loading device 210 can be moved along the catheter body 292 without being impeded by any part of guidewire section 220. In some embodiments, the device 210 can be moved from an initial proximal position towards the distal end 290 of the catheter 280 until at least a portion of the curved section 288 of the catheter 280 proximate the distal end 290 is positioned within the receiver, as illustrated in FIG. 2B. In the illustrated embodiment, the portion of the curved section 288 positioned within the receiver 242 is straightened sufficiently to facilitate insertion of the proximal end of guidewire 270 into catheter lumen 284. This straightening, in one or more embodiments, may aid the clinician in directing the guidewire 270 into the lumen 284 of the catheter 280 by aligning axis 286 of lumen 284 with axis 274 of guidewire 270 and also by reducing friction that would be encountered if the straight proximal end of guidewire 270 were to be pushed into curved distal section 288 of catheter 280 without first straightening section 288. In this context, curved section 288 need not be perfectly straightened to facilitate insertion of the proximal end of guidewire 270 into catheter lumen 284, and the degree of useful straightness of section 288 depends on variables such as the diameter of lumen 284, the diameter and stiffness of the proximal end of guidewire 270, and the amount of friction between these two components. In one example, it was found that a distal catheter section 288 held in a curve radius of 0.40 inch or larger required an acceptably low amount of manual effort to insert the proximal end of a 0.014 inch medical guidewire into open distal end 290 of the catheter.

As described herein, the guidewire section 220 can be bent about the rotation axis 262 relative to the catheter section 240 between a first position (shown in FIG. 2B) and the second position (shown in FIG. 2A). When guidewire section 220 is in the first position, the device 210 is configured such that the longitudinal axis 274 of a guidewire 270 positioned in the channel 222 is aligned with the longitudinal axis 286 of the lumen 284 of the catheter 280 positioned in the receiver 242 as is shown in FIG. 2B. Further, as shown in FIG. 2A, the longitudinal axis 274 of the guidewire 270 is not aligned with the longitudinal axis 286 of the lumen 284 of the catheter 280 when the guidewire section 220 is in the second position.

In general, any suitable technique can be used with the catheter loading devices described herein. Referring to catheter loading device 210 of FIGS. 2A-C, in one exemplary embodiment, a clinician receives the catheter 280 that includes the catheter loading device 210 mounted on the elongate catheter body 292 such that a portion of the catheter body is within the receiver 242 of the catheter section 240 of the loading device. Alternatively, the loading device can be received separately from the catheter. In such cases, device 210 can be threaded onto catheter body 292 over distal tip portion 282, or device 310 having slit 352 can be side-mounted onto the catheter as described below. The loading device 210 is oriented on catheter 280 such that a distal portion of catheter 280 extends distally from receiver 242 and a proximal portion of catheter 280 extends proximally from receiver 242.

To prepare for use, catheter loading device 210 is moved distally along the elongate catheter body 292 until the catheter distal end 290 is in a loading position, e.g. a position for receiving guidewire proximal end 272 in the open distal end of catheter lumen 248, as shown in FIG. 2B. In the loading position, catheter distal end 290 may be located proximate hinge 260. Catheter distal end 290 may be aligned with or abutting hinge end 228 of distal portion 220, especially if the catheter has a curved distal section 288. Alternatively, tests have shown that, when loading a 0.014 inch diameter medical guidewire, catheter distal end 290 may be spaced up to 2 mm away from hinge end 228, and may be positioned within receiver 242. In loading devices 10 and 310 having recess 30, 330 respectively, the loading position for the catheter places catheter distal 90, 290 within recess 30, 330 and perhaps abutting the step between recess 30, 330 and the remainder of channel 22, 322. In embodiments where catheter 280 includes a curved section 288, at least a portion of the curved section is positioned within receiver 242 to constrain or temporarily straighten at least the portion of curved section 288 while it is positioned within receiver 242.

In some embodiments, prior to or concurrently with moving device 210 along the elongate catheter body 292, guidewire section 220 can be bent or flexed, e.g. rotated on hinge axis 262 relative to the catheter section 240 from the first position to the second position such that guidewire section 220 does not contact catheter 280 as device 210 is moved along the catheter body. This enables the clinician to more easily move device 210 along catheter body 292.

When the catheter distal end 290 is in the desired loading position, guidewire section 220 can be rotated relative to the catheter section 240 about the rotation axis 262 from the second position to the first position as shown in FIG. 2B such that the longitudinal axis 274 of the guidewire 270 is aligned with the longitudinal axis 286 of the lumen 284 of the catheter 280. In embodiments wherein hinge 260 is a living hinge biased to position guidewire section 220 in the first position, the transition from the second position to the first position can be achieved by simply permitting device 210 to resume its biased or natural configuration.

Once device 210 is in the first position and catheter distal end 290 is in the desired loading position, proximal end 272 of guidewire 270 is positioned in channel 222 of the guidewire section 220 of the device 210. The proximal end 272 of the guidewire 270 is then directed into the lumen 284 of the catheter 280. Guidewire proximal end 272 can be fully inserted through catheter lumen 284 to exit therefrom either at the proximal end of an over-the-wire (OTW) type catheter or from a side port of a rapid exchange (RX) type catheter.

Figure 3:
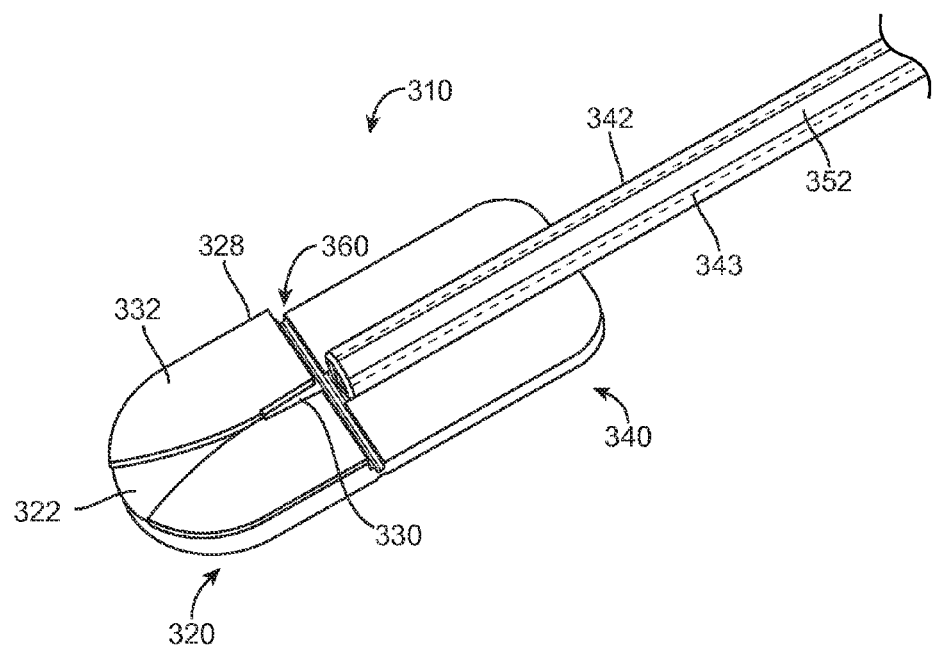
FIG. 3 is a perspective view of another embodiment of a catheter loading device.

In an alternative embodiment shown as device 310 in FIG. 3, a guidewire section 320 is rotatably connected to a catheter section 340 by a hinge 360. All of the design considerations and possibilities regarding the guidewire section 20, the catheter section 40, and the hinge 60 of the embodiment illustrated in FIGS. 1A-E apply equally to the guidewire section 320, the catheter section 340, and the hinge 360 of the embodiment illustrated in FIG. 3. In device 310, an elongate recess 330 is formed in a surface 332 of the guidewire section 320 adjacent the proximal end 328 of the guidewire section 320. Similar to recess 30, recess 330 is aligned with and may be considered to be a proximal portion of channel 322. Recess 330 is sized and shaped for receiving the distal tip of a catheter. In the loading position of this embodiment (not shown), the catheter distal tip extends distally from receiver 342 across hinge 360 into recess 330 of guidewire section 320.

Once proximal end 272 of guidewire 270 is loaded into lumen 284 of the catheter 280, the catheter loading device 210 can be slid proximally along catheter body 292 to the catheter proximal end 294 or at least far enough along the catheter to be out of the clinician's way during the catheterization procedure. In embodiments where catheter 280 includes a curved section 288, sliding device 210 proximally from section 288 releases the straightening constraint provided thereto by receiver 242. However, with guidewire 270 loaded into catheter lumen 284, the guidewire itself may straighten curved section 288. The extent of this guidewire straightening will depend upon the stiffness of the selected type of guidewire and particularly upon the stiffness of the portion of the guidewire disposed within curved section 288 as will be understood by persons knowledgeable in the field of catheters. The clinician can direct the catheter along the guidewire until it reaches the desired site within a patient.

Returning to the embodiment of FIG. 3, receiver 342 of catheter loading device 310 may also include a slit or slot 352 such that the device 310 can be mounted or removed from a catheter (e.g., catheter 280 of FIG. 2) by transversely passing the catheter through the slit or slot. The slit 352 can have any suitable shape and dimensions such that the catheter can be moved laterally through the slit. In some embodiments, the receiver 342 can include materials that are resilient, and the slit 352 can be sized such that it has a width slightly smaller than a diameter of the catheter. In such embodiments, the catheter can still move through the slit 352 as the receiver 342 will flex or open as device 310 is forced onto or pulled away from the catheter. Slit 352 allows the clinician to remove device 310 completely from the catheter rather than slide the device proximally along the length of the catheter. Receiver lumen 343 may be sized to permit device 310 to slide along a catheter, or receiver lumen 343 may be sized with a slight interference fit with the catheter to frictionally hold device 310 in a desired position on the catheter.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A catheter loading device, comprising:
    a guidewire section having a channel configured to receive a guidewire, wherein the channel extends along a channel axis from a free end of the guidewire section towards a proximal end of the guidewire section, wherein a width of the channel adjacent the proximal end thereof is sufficiently narrow to align the guidewire with the channel axis;
    a catheter section comprising a tubular receiver having a lumen configured such that a catheter having a lumen receptive to the guidewire may be slidably disposed therethrough and extending from proximal and distal ends of the receiver lumen, wherein the receiver distal end is connected to a distal end of the catheter section via a tab and the receiver extends along a receiver axis from the distal end of the catheter section to or beyond a free end of the tab; and
    a hinge rotatably connecting the proximal end of the guidewire section to the distal end of the catheter section, wherein the hinge defines a rotation axis transverse to the receiver axis;
    wherein the guidewire section is rotatable relative to the catheter section about the rotation axis between a first position and a second position;
    wherein, when the guidewire section is in the first position, a longitudinal axis of the guidewire positioned in the channel is aligned with a longitudinal axis of the lumen of the catheter positioned in the receiver, and
    wherein, when the guidewire section is in the second position, the longitudinal axis of the guidewire positioned in the channel is not aligned with the longitudinal axis of the lumen of the catheter positioned in the receiver such that the guidewire section does not contact the catheter when the loading device is slid proximally along the catheter.

2. The device of claim 1, wherein at least a portion of the channel has a width measured in a direction parallel to the rotation axis, the width tapering in a direction along the channel axis from the free end of the guidewire section to the proximal end of the guidewire section.

3. The device of claim 2, wherein the channel further comprises, at the proximal end of the guidewire section, a recess configured to receive a distal end of a catheter.

4. The device of claim 3, wherein the channel and the recess are formed in a surface of the guidewire section, and further wherein the recess comprises a second depth greater than the first depth.

5. The device of claim 4, wherein the first depth of the channel and the second depth of the recess are selected such that, when the guidewire section is in the first position and a distal end of the catheter is positioned in the recess, the longitudinal axis of the guidewire positioned in the channel is aligned with the longitudinal axis of the lumen of a catheter.

6. The device of claim 1, wherein the channel is formed into a surface of the guidewire section and the receiver is disposed on a surface of the catheter section, and wherein a plane containing the surface of the guidewire section is substantially parallel to a plane containing the surface of the catheter section when the guidewire section is in the first position.

7. The device of claim 1, wherein the hinge is biased to position the guidewire section in the first position.

8. The device of claim 1, wherein the tubular receiver comprises a slit or slot configured such that the loading device can be mounted onto or removed from the catheter by transversely passing the catheter through the slit or slot.

9. A catheter comprising:
an elongate catheter body having a lumen extending therethrough from an open distal end of the catheter, the lumen having a longitudinal axis; and
a loading device mounted about the catheter body, wherein the device comprises:
a guidewire section having a channel configured to receive a guidewire, wherein the channel extends along a channel axis between a free end of the guidewire section and a proximal end of the guidewire section, wherein a width of the channel adjacent the proximal end thereof is sufficiently narrow to align the guidewire with the channel axis;
a catheter section comprising a tubular receiver having a lumen configured such that the catheter having a lumen receptive to the guidewire may be slidably disposed therethrough and extending from proximal and distal ends of the receiver lumen, wherein the receiver distal end is attached to a distal end of the catheter section via a tab and the receiver extends along a receiver axis from a distal end of the catheter section to or beyond a free end of the tab; and
a hinge rotatably connecting the proximal end of the guidewire section to the distal end of the catheter section, the hinge defining a rotation axis transverse to the receiver axis;
wherein the guidewire section is rotatable about the rotation axis relative to the catheter section between a first position and a second position;
wherein, when the guidewire section is in the first position and the catheter is positioned in the receiver and the guidewire is positioned in the channel, a longitudinal axis of the guidewire is aligned with the longitudinal axis of the catheter lumen, and
wherein, when the guidewire section is in the second position and the catheter is positioned in the receiver and the guidewire is positioned in the channel the longitudinal axis of the guidewire is not aligned with the longitudinal axis of the lumen of the catheter such that the guidewire section does not contact the catheter when the loading device is slid proximally along the catheter.

10. The catheter of claim 9, wherein the catheter body comprises a curved section proximate the distal end of the catheter.

11. The catheter of claim 10, wherein the curved section of the catheter comprises a helical shape.

12. The catheter of claim 9, wherein the tubular receiver is configured to straighten at least a portion of a curved section of the catheter body.

13. A method, comprising:
receiving a catheter having an elongate catheter body and a guidewire lumen extending therethrough from an open catheter distal end;
receiving a loading device comprising
a guidewire section having a channel configured to receive a guidewire, wherein the channel extends along a channel axis between a free end of the guidewire section and a proximal end of the guidewire section, wherein a width of the channel adjacent the proximal end thereof is sufficiently narrow to align the guidewire with the channel axis; and
a catheter section having a tubular receiver having a lumen configured such that the catheter having a lumen receptive to the guidewire may be slidably disposed therethrough and extending from proximal and distal ends of the receiver lumen, wherein the receiver distal end is attached to a distal end of the catheter section via a tab and the receiver extends along a receiver axis from a distal end of the catheter section to or beyond a free end of the tab;
wherein a proximal end of the guidewire section is connected to a distal end of the catheter section by a hinge that defines a rotation axis transverse to the receiver axis such that the guidewire section is rotatable about the rotation axis relative to the catheter section between a first position and a second position;
positioning the loading device on the catheter such that the catheter body is disposed within the receiver and the catheter distal end is located proximate the hinge;
positioning a proximal end of a guidewire in the channel;
directing the proximal end of the guidewire into the open distal end of the catheter; and
rotating the guidewire section relative to the catheter section about the rotation axis from the first position to a second position before sliding the device along the catheter body such that the guidewire section does not contact the catheter body as the catheter loading device slides along the catheter body.

14. The method of claim 13, wherein positioning the loading device further comprises sliding the loading device along the catheter body.

15. The method of claim 14, wherein the hinge biases the guidewire section in the first position, the method further comprising rotating the guidewire section relative to the catheter section about the rotation axis from the first position to a second position before sliding the device along the catheter body such that the guidewire section does not contact the catheter body as the catheter loading device slides along the catheter body.

16. The method of claim 13, wherein receiving a loading device further comprises the loading device being mounted about a portion of the catheter body while receiving the catheter.

17. The method of claim 13, wherein positioning the loading device further comprises moving the tubular receiver of the loading device along the catheter body such that at least a portion of a curved section of the catheter body proximate the distal end of the catheter is positioned within the tubular receiver, thereby straightening the portion of the curved section of the catheter positioned within the tubular receiver.

18. The method of claim 13, wherein the channel of the guidewire section further comprises a recess adjacent the proximal end of the guidewire section, the recess being configured to receive a distal end of a catheter.

\* \* \* \* \*